(12) United States Patent
Maurer et al.

(10) Patent No.: US 7,842,247 B2
(45) Date of Patent: Nov. 30, 2010

(54) SAMPLE HOLDER FOR DYNAMIC LIGHT SCATTERING

(75) Inventors: Elisabeth Maurer, Vancouver (CA); Georg Maurer, Vancouver (CA); Keddie Brown, Vancouver (CA)

(73) Assignee: Canadian Blood Services, Ottawa, Ontario (CA)

( * ) Notice: Subject to any disclaimer, the term of this patent is extended or adjusted under 35 U.S.C. 154(b) by 1277 days.

(21) Appl. No.: 11/208,080

(22) Filed: Aug. 19, 2005

(65) Prior Publication Data

US 2007/0041877 A1  Feb. 22, 2007

(51) Int. Cl.
| | |
|---|---|
| *B01L 3/00* | (2006.01) |
| *B01L 9/00* | (2006.01) |
| *G01N 21/01* | (2006.01) |
| *G01N 15/02* | (2006.01) |
| *G01N 21/00* | (2006.01) |
| *F25B 29/00* | (2006.01) |
| *G01N 31/00* | (2006.01) |

(52) U.S. Cl. .................. 422/102; 422/99; 422/104; 436/10; 435/287.1; 356/244; 356/336; 356/337; 165/48.1; 165/61; 165/80.3

(58) Field of Classification Search .................. 422/99, 422/102, 104; 436/10; 435/287.1; 356/244, 356/336, 337; 165/80.3, 48.1, 61
See application file for complete search history.

(56) References Cited

U.S. PATENT DOCUMENTS 4,007,013 A   2/1977   Kotacka

| 4,208,127 A | 6/1980 | Hufenreuter |
|---|---|---|
| 4,274,740 A | 6/1981 | Eidenschink et al. |
| 4,278,437 A | 7/1981 | Haggar |
| D271,335 S | 11/1983 | Simons |

(Continued)

FOREIGN PATENT DOCUMENTS

| CA | 1242595 | 10/1988 |
|---|---|---|
| CA | 1247399 | 12/1988 |

OTHER PUBLICATIONS

"Temperature-Regulated Cuvette Holder"; Ocean Optics 2004; Making Waves; Spectrometers & Accessories; p. 77.
Product Literature from Wyatt Technology Coproration regarding "Wyatt's DynaPro".
Product Literature from Becher Coulter regarding "Coulter N4 Plus".

*Primary Examiner*—Jill Warden
*Assistant Examiner*—Dean Kwak
(74) *Attorney, Agent, or Firm*—Olson & Cepuritis, Ltd.

(57) ABSTRACT

A sample holder holds various sizes of capillaries or cuvettes for use in dynamic light scattering (DLS) or quasi-elastic light scattering (QELS), such as in DLS of fluid samples such as platelet solutions, whole blood, colloids or the like. The sample holder has a base with a stationary backing member and a sliding, rail-mounted clamping member that is magnetically biased toward the backing member. The sample holder has Peltier-type thermoelectric heating/cooling elements that extend the full height of the clamping and backing members to optimize heat transfer efficiency. The sample holder further includes horizontal slots that enable collection of scattered light from various angles around the device. Finned heat sinks are mounted above and below the horizontal slots on the outwardly facing surfaces of the backing and clamping members to stabilize the temperature of the fluid sample in the sample holder without interfering with incident or scattered light.

36 Claims, 5 Drawing Sheets

U.S. PATENT DOCUMENTS

| | | |
|---|---|---|
| 4,975,237 A | 12/1990 | Watling |
| 4,991,601 A | 2/1991 | Kasai et al. |
| 5,092,674 A | 3/1992 | Garner |
| 5,530,540 A | 6/1996 | Wyatt et al. |
| 5,674,457 A | 10/1997 | Williamson et al. |
| 5,733,507 A | 3/1998 | Zakim |
| 5,817,519 A | 10/1998 | Zelmanovic et al. |
| 5,869,346 A | 2/1999 | Xiaoming et al. |
| 5,900,132 A | 5/1999 | Keenan et al. |
| 5,907,399 A | 5/1999 | Shirasawa et al. |
| 6,004,818 A | 12/1999 | Freilich et al. |
| 6,016,193 A | 1/2000 | Freeman et al. |
| 6,043,871 A | 3/2000 | Solen et al. |
| 6,055,050 A | 4/2000 | Skiffington |
| 6,188,474 B1 | 2/2001 | Dussault et al. |
| D442,287 S | 5/2001 | Pogorzelski |
| 6,228,652 B1 | 5/2001 | Rodriguez et al. |
| 6,239,875 B1 | 5/2001 | Verheijen |
| 6,249,344 B1 | 6/2001 | Virag |
| 6,266,139 B1 | 7/2001 | Mannhardt |
| 6,375,027 B1 | 4/2002 | Thomas et al. |
| 6,399,026 B1 | 6/2002 | Karrai |
| 6,488,892 B1 | 12/2002 | Burton et al. |
| 6,618,144 B1 | 9/2003 | Reed |
| 6,774,994 B1 | 8/2004 | Wyatt et al. |
| 6,798,520 B2 | 9/2004 | Lafferty |
| 6,867,857 B2 | 3/2005 | Hobbs |
| 2002/0009397 A1 | 1/2002 | Hirono et al. |
| 2002/0167667 A1 | 11/2002 | Samsoondar et al. |
| 2004/0233423 A1 | 11/2004 | Nakayama et al. |
| 2005/0094127 A1 | 5/2005 | O'Mahony et al. |

SAMPLE HOLDER FOR DYNAMIC LIGHT SCATTERING

CROSS-REFERENCE TO RELATED APPLICATIONS

This is the first application filed for the present invention.

MICROFICHE APPENDIX

Not Applicable.

TECHNICAL FIELD

The present invention relates generally to optical analysis of fluids, colloidal dispersions or suspensions and, in particular, to sample-holding devices for dynamic light scattering (DLS) or quasi-elastic light scattering (QELS).

BACKGROUND OF THE INVENTION

Dynamic light scattering (DLS), which is also known as quasi-elastic light scattering (QELS), is an optical analysis technique that is well known in the art. An optical source such as laser light is focused into the sample. Light scatters when it hits particles suspended in the fluid, such as platelets suspended in solution. The scattered light is collected by light collectors disposed at specific angles relative to the incident light. As is known in the art, the scattered light fluctuates due to Brownian motion of the particles in solution. Using algorithms that are known in the art, these fluctuations of scattered light are then correlated to the particles' mean size and shape which are expressed in terms of hydrodynamic radius.

To perform dynamic light scattering on a fluid sample, the fluid sample is contained within a translucent container (e.g. a capillary or cuvette) that is, in turn, held by a sample holder, also known as a capillary holder or cuvette holder.

A number of sample holders and DLS-type apparatuses having sample-holding compartments are known in the art, for example the Coulter N4 Plus™ from Beckman Coulter, Inc. of Fullerton, Calif. and the DynaPro Titan™ from Wyatt Technology Corporation of Santa Barbara, Calif.

Some sample-holding devices are described in U.S. Patent Application 2005/0094127 (O'Mahony et al.) entitled CUVETTE APPARATUS AND SYSTEM FOR MEASURING OPTICAL PROPERTIES OF A LIQUID SUCH AS BLOOD; U.S. Pat. No. 6,016,193 (Freeman et al.) entitled CUVETTE HOLDER FOR COAGULATION ASSAY TEST; U.S. Pat. No. 6,249,344 (Virag) entitled METHOD AND APPARATUS FOR SEDIMENTATION AND OPTICAL EXAMINATION OF PARTICLES SUSPENDED IN A FLUID, FURTHER A CUVETTE FOR ACCOMPLISHING SAID METHOD; U.S. Design Pat. No. D442,287 (Pogorzelski) entitled CUVETTE HOLDER; U.S. Design Pat. No. D271,335 (Simons) entitled CUVETTE HOLDER; U.S. Pat. No. 4,208,127 (Hufenreuter) entitled CUVETTE HOLDER; U.S. Pat. No. 6,488,892 (Burton et al.) entitled SAMPLE-HOLDING DEVICES AND SYSTEMS; U.S. Pat. No. 6,399,026 (Karrai) entitled SAMPLE HOLDER APPARATUS; U.S. Pat. No. 6,266,139 (Mannhardt) entitled CAPILLARY TUBE HOLDER; U.S. Pat. No. 4,278,437 (Haggar) entitled FLUID SPECIMEN HOLDER FOR BIOLOGICAL FLUID TESTING; U.S. Pat. No. 6,239,875 (Verheijen) entitled PHOTOMETRIC MEASURING SYSTEM AND A HOLDER FOR SUCH A SYSTEM; U.S. Pat. No. 6,055,050 (Skiffington) entitled PHOTOMETER AND TEST SAMPLE HOLDER FOR USE THEREIN, METHOD AND SYSTEM; U.S. Patent Application 2004/0233423 (Nakayama et. al.) entitled SAMPLE HOLDER FOR SPECTRUM MEASUREMENT AND SPECTROPHOTOMETER; U.S. Pat. No. 5,900,132 (Keenan et al.) entitled CAPILLARY HOLDER; U.S. Pat. No. 5,733,507 (Zakim) entitled BIOLOGICAL CELL SAMPLE HOLDER FOR USE IN INFRARED AND/OR RAMAN SPECTROSCOPY ANALYSIS HOLDER; U.S. Pat. No. 6,188,474 (Dussault et al.) entitled OPTICAL SPECTROSCOPY SAMPLE CELL; U.S. Pat. No. 5,674,457 (Williamson et al.) entitled CAPILLARY MICROCUVETTE; Canadian Patent 1,247,399 (Wyatt et al.) entitled SAMPLE CELL FOR LIGHT SCATTERING MEASUREMENTS; Canadian Patent 1,242,595 (Phillips et al.) entitled SAMPLE CELL FOR LIGHT SCATTERING MEASUREMENTS; and U.S. Pat. No. 5,530,540 (Wyatt et al.) entitled LIGHT SCATTERING MEASUREMENT CELL FOR VERY SMALL VOLUMES.

However, to the extent of Applicant's knowledge, each of these prior-art sample holders is only designed to hold a specific type of container (i.e. either a round capillary or a square cuvette) and furthermore is only designed to only hold a container of a specific size or of a very limited size range. Accordingly, it would be highly desirable to provide a sample holder that redressed this deficiency.

Moreover, many of these prior-art sample holders include means for heating and/or cooling the fluid sample in order to collect DLS measurements at different temperatures. However, these prior-art temperature-controlled sample holders are not designed for efficient and uniform heat transfer because they must provide optical access for both the incident light and the scattered light. In other words, heating or cooling elements are located inefficiently (such as beneath the container) in order to ensure that there is adequate optical access. The prior-art designs have in general failed to optimize both optical access and heat transfer. It would therefore be highly desirable to provide a sample holder that enables efficient and uniform heat transfer without unduly compromising optical access to the sample.

SUMMARY OF THE INVENTION

It is therefore an object of the present invention to provide a sample holder that overcomes at least one of the deficiencies of the prior art. The sample holder (or sample-holding device) has a base including a stationary upright wall or "backing member". A movable upright member or "clamping member" can be displaced relative, e.g. by sliding over a rail, so as to gently clamp or grip a capillary, cuvette, tube or other fluid container between the two members or walls. This design facilitates the loading, holding and unloading of variously sized capillaries, cuvettes or other such fluid sample containers. The sample holder further includes heating/cooling elements mounted on each wall or upright member. In one embodiment, the heating/cooling elements are mounted between the wall (or upright member) and a respective grooved, heat-conductive plate which has opposed, inwardly facing grooves for gripping the fluid container to preferably hold the container in a substantially vertical orientation. The heating/cooling elements can be made to extend the full height of the plates and walls (upright members) to provide efficient and uniform heat transfer to and from the fluid sample in the sample holder. In one embodiment, the sample holder includes finned heat sinks and fans to facilitate cooling of the sample. In order to enhance optical access to the fluid sample, substantially horizontal slots are provided in the walls (upright members), in the heating/cooling elements and in the plates.

This sample holder can therefore be integrated into a dynamic light scattering (DLS) system for collecting scattered light from a variety of locations around the sample. Therefore, a DLS system using this sample holder can operate with a single light source, such as a single laser diode, while collecting scattered light by deploying a plurality of light collectors at various locations around the sample holder. This versatile, easy-to-use and efficient sample holder greatly facilitates DLS/QELS or other optical analysis techniques for analyzing platelet solutions, whole blood or other colloids or colloidal dispersions.

Accordingly, one aspect of the invention therefore provides a sample holder for holding a fluid container for performing optical analysis of a fluid sample contained within the container. The sample holder includes a base having an upright backing member and a movable clamping member that moves relative to the backing member between an open, retracted position, in which the clamping member no longer contacts the container, and a closed, holding position, in which the clamping member presses against the container to lightly clamp the container between the clamping member and the backing member whereby the container is immobilized for optical analysis of the fluid sample in the container.

In one embodiment, the backing member and the clamping member include, respectively, first and second pairs of upper and lower grooved plates facing each other in a generally parallel arrangement and having opposed, substantially vertical grooves for holding the fluid container in a substantially vertical orientation.

In another embodiment, the base includes a rail for guiding the movable clamping member along a displacement axis that is substantially perpendicular to the backing and clamping members.

In yet another embodiment, the clamping member includes a magnet for magnetically biasing the clamping member toward the backing member.

In a further embodiment, the sample holder includes a first pair of upper and lower heating/cooling elements connected to an inwardly facing surface of the backing member, the first pair of heating/cooling elements being capable of transferring heat to the fluid sample in the container; a first pair of heat-conductive plates connected to inwardly facing surfaces of the first pair of heating/cooling elements for conducting heat to or from the fluid sample in the container; a second pair of heating/cooling elements connected to an inwardly facing surface of the movable clamping member, the second pair of heating/cooling elements being capable of transferring heat to or from the fluid sample in the container; and a second pair of heat-conductive plates connected to inwardly facing surfaces of the second pair of heating/cooling elements for conducting heat to or from the fluid sample in the container.

Another aspect of the invention provides a holding device for holding a container capable of containing a fluid sample for undergoing optical analysis. The holding device includes a base having a fixed, upright wall and a movable upright member capable of moving relative to the wall between a retracted position, in which the movable upright member and the wall are separated by a distance greater than an outer diameter of the container, and a gripping position, in which the container is held between the movable upright member and the wall.

In one embodiment, the base includes a rectilinear rail for guiding the movable upright member when sliding relative to the wall.

In another embodiment, the wall and movable member each have substantially horizontal slots for providing optical access to the fluid sample in the container.

In a further embodiment, the holding device further includes a first pair of heating/cooling elements disposed on an inwardly facing surface of the wall and a second pair of heating/cooling elements disposed on an inwardly facing surface of the movable member.

In yet a further embodiment, the holding device includes a first pair of heat-conductive plates connected to inwardly facing surfaces of the first pair of heating/cooling elements, the first pair of plates having an inwardly facing groove for gripping the container over a substantial surface of the container for efficiently conducting heat to or from the container; and a second pair of heat-conductive plates connected to inwardly facing surfaces of the second pair of heating/cooling elements, the second pair of plates having an inwardly facing groove for gripping the container over a substantial surface of the container for efficiently conducting heat to or from the container.

Another aspect of the invention provides a system for dynamic light scattering of a fluid sample contained within a container. The system includes a light source for directing a beam of light at the fluid sample and a sample-holding device. The device has a base having a fixed, upright wall and a movable upright member capable of moving relative to the wall between a retracted position, in which the movable upright member and the wall are separated by a distance greater than an outer diameter of the container, and a gripping position, in which the container is held between the movable upright member and the wall. The system further includes a light collector for collecting light scattered by the fluid sample and a correlating means for correlating collected scattered light to size and shape of particles suspended in a solution in the container.

In one embodiment, the wall and the movable member comprise horizontal slots to provide optical access to the fluid sample whereby the light source and light collector can be positioned at one of a plurality of positions around the device.

In another embodiment, the system includes a single light source and a plurality of light collectors deployed around the sample-holding device to collect light scattered by the fluid sample.

In a further embodiment, the light source includes a laser diode and the light collector includes at least one optical fiber for capturing scattered photons, the optical fiber being connected to a single-photon counter for generating and transmitting TTL (transistor-transistor logic) pulses to the correlating means.

In yet a further embodiment, the system further includes an L-shaped bracket for supporting either a single-mode polarization-maintaining optical fiber or a multimode fiber connected to a laser diode and at least one other L-shaped bracket for supporting at least one other optical fiber connected to a single-photon counting module.

In yet a further embodiment, the system further includes a first fan for blowing air over a finned portion of a heat sink affixed to the wall and a second fan for blowing air over a finned portion of a heat sink affixed to the movable member.

BRIEF DESCRIPTION OF THE DRAWINGS

Further features and advantages of the present invention will become apparent from the following detailed description, taken in combination with the appended drawings, in which.

It should be noted that throughout the appended drawings, like features are identified by like reference numerals.

DETAILED DESCRIPTION OF PREFERRED EMBODIMENTS

Figure 1:
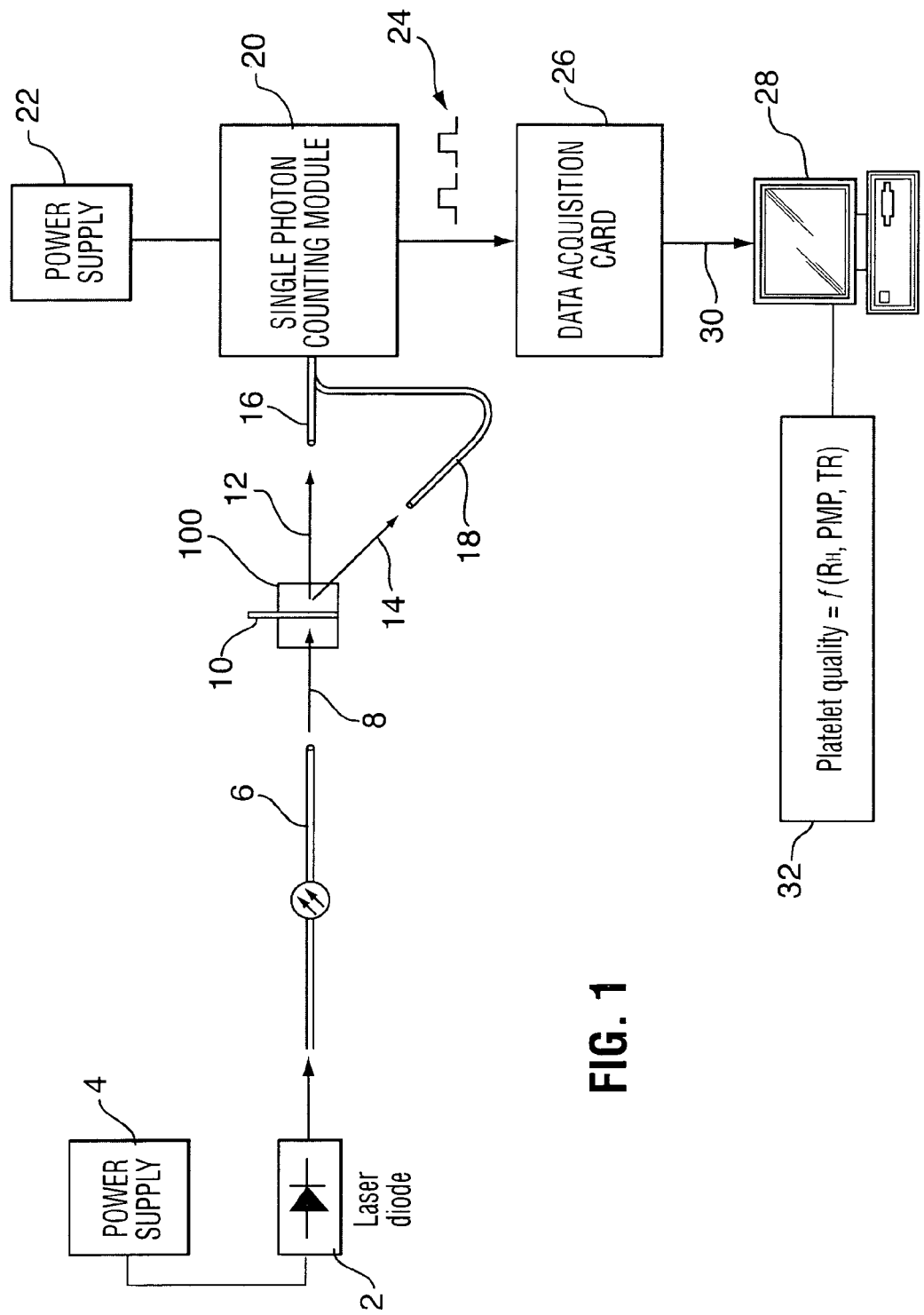
FIG. 1 is a schematic view of a DLS system having a sample holder in accordance with an embodiment of the present invention.

FIG. 1 is a schematic view of a system for dynamic light scattering (DLS), which is also known as quasi-elastic light scattering (QELS). As shown in FIG. 1, the system has a light source such as, for example, a laser diode 2 which is powered by a power source, as is well known in the art. The laser diode 2 generates and emits a beam of laser light into a length of optical fiber 6. The laser preferably generates light at 635 nm although other wavelengths could be used, as would be appreciated by those of ordinary skill in the art. As is also known in the art, the intensity of the laser beam can be adjusted using an adjustable neutral density filter (or by using an attenuator in the fiber) which allows the laser to be operated at maximum power while curtailing the intensity of the incident light. This reduces multiple scattering and other undesirable optical effects that arise when the intensity of the incident light is too high. The optical fiber can be single-mode, polarization-maintaining optical fiber which, as is well known in the art, prevents the polarization from drifting when the light propagates through the optical fiber or, alternatively, multimode fiber can be utilized. As is known in optics, polarization-maintaining fibers can be made using fibers of noncircular cross-section or by making the propagation medium of the fibers anisotropic such as, for example, by stressing the fibers in a specific direction.

As shown in FIG. 1, the polarized laser light emerges from the optical fiber 6 and travels a short distance through the air (although it should be expressly understood that the distances shown in FIG. 1 are not meant to be representative or proportional to actual distances). This incident light impinges on a fluid sample (e.g. platelets in solution, whole blood, or other colloids or colloidal dispersions) contained with a transparent or translucent container 10 (e.g. a capillary, cuvette, tube or like structure) held by a sample holder 100 in accordance with embodiments of the present invention. The sample holder 100 will be described in greater detail below with reference to FIGS. 3-5.

As shown in FIG. 1, the incident light scatters when photons strike particles suspended in the solution. The scattered light 12, 14 scatters in various directions away from the fluid sample. A portion of this scattered light is collected by light collectors 16, 18, which are preferably optical fibers connected to a single-photon counting module 20 powered by its own power supply 22. In a preferred embodiment, the single-photon counting module 20 generates TTL pulses (transistor-transistor logic pulses) 24 and transmits these TTL pulses 24 to a data acquisition card 26. The data acquisition card 26 digitizes the TTL pulses and communicates the "raw data" to a software correlator running on a laptop or other computer 28. This raw data is communicated via a universal serial bus (USB) 30 or other data bus or connector. Alternatively, the data acquisition card 26 can be installed within the computer 28. Together, the data acquisition card 26, computer 28 and software correlator constitute a "correlating means", as this expression is used in the present specification. Alternatively, the correlating means could utilize a hardware correlator (e.g. a multi-tau correlator) instead of the data acquisition card. The hardware correlator would generate and communicate a correlation function to the computer, although the data acquisition card and software correlator are preferred as it has been found to be more accurate. Correlating the observed speckle pattern that arises due to Brownian motion with particle size (i.e. hydrodynamic radius) is based on the Stokes-Einstein equation, as is known in the art.

Figure 2:
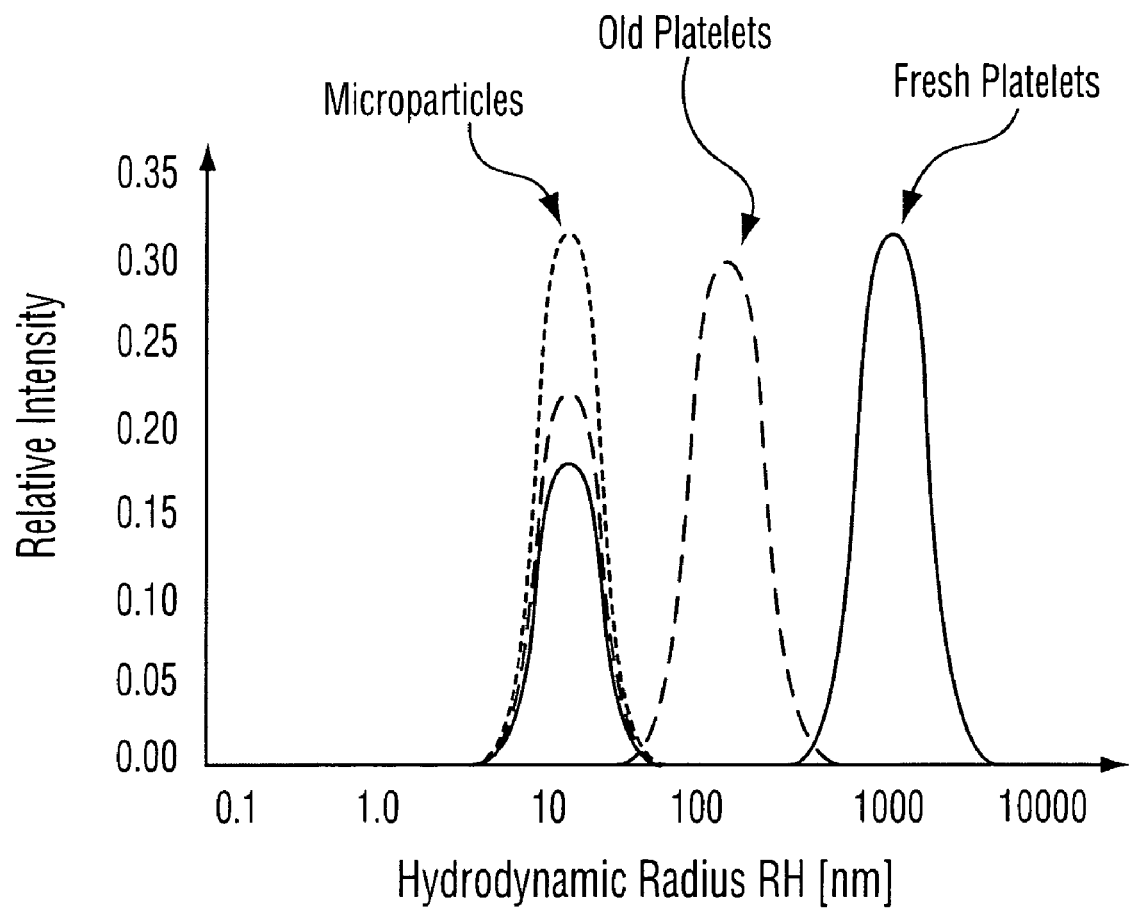
FIG. 2 is a graph plotting a distribution of hydrodynamic radii as a function of light intensity obtained from a DLS "speckle pattern" of platelets and platelet-derived microparticles (PMPs) in solution as could be obtained using the DLS system shown in FIG. 1.

The computer 28 (running the software correlator) generates a correlation function and then generates a size distribution plot, such as the one shown in FIG. 2, for graphical presentation to a researcher or other end-user. Alternatively, size distribution data can be presented in tabular form or in any other intelligible manner.

As depicted in FIG. 2, the size distribution plot shows a representative distribution of hydrodynamic radii for platelets and microparticles in a fresh platelet concentrate (solid line), platelets and microparticles in an old platelet concentrate (dashed line) and platelet-derived microparticles alone (PMPs) (dotted line) although it should be expressly understood that the hydrodynamic radii, relative intensities and particle distributions shown are not meant to represent actual values or distributions. The hydrodynamic radii are calculated from the DLS "speckle pattern", as is known in the art. The size distribution plot readily enables researchers, technicians or other end-users to evaluate platelet quality and viability by virtue of the size distribution. New platelets can be distinguished from old platelets because the mean hydrodynamic radius (RH) of platelets diminishes with age. Likewise, platelet-derived microparticles (PMPs) serve as a second useful indicator of age (and diminishing platelet quality) because PMPs form, or "bud off", as platelets degrade over time. Temperature response is yet another means of evaluating platelet age and quality: fresh platelets can be prepared such that they are more (or less) resistant to temperature variation than old platelet concentrates.

In one embodiment, the computer 28 implements a computational matrix 32 for analyzing platelet quality and viability based on three independent factors, namely (i) the mean hydrodynamic radius of the platelets, (ii) the relative number of PMPs and (iii) the platelet response to temperature cycling. As shown in FIG. 1, the computational matrix 32 quantifies platelet quality as a function of mean hydrodynamic radius (RH), PMP concentration, and temperature response (TR). The computational matrix 32 therefore enables automated platelet scoring because the system can simultaneously measure and input into the computational matrix all three of these independent parameters, thus providing very high analytic sensitivity for platelet quality determinations. This methodology is described in detail in applicant's co-pending U.S. patent application Ser. No. 10/925,779 (Maurer) filed Aug. 24, 2004 and entitled METHOD FOR DETERMINATION OF PLATELETS QUALITY, which is hereby incorporated by reference.

It should be expressly understood that this system can be used not only for DLS analysis of platelets in solution, but also for analyzing whole blood or other colloids or colloidal dispersions.

Figure 3:
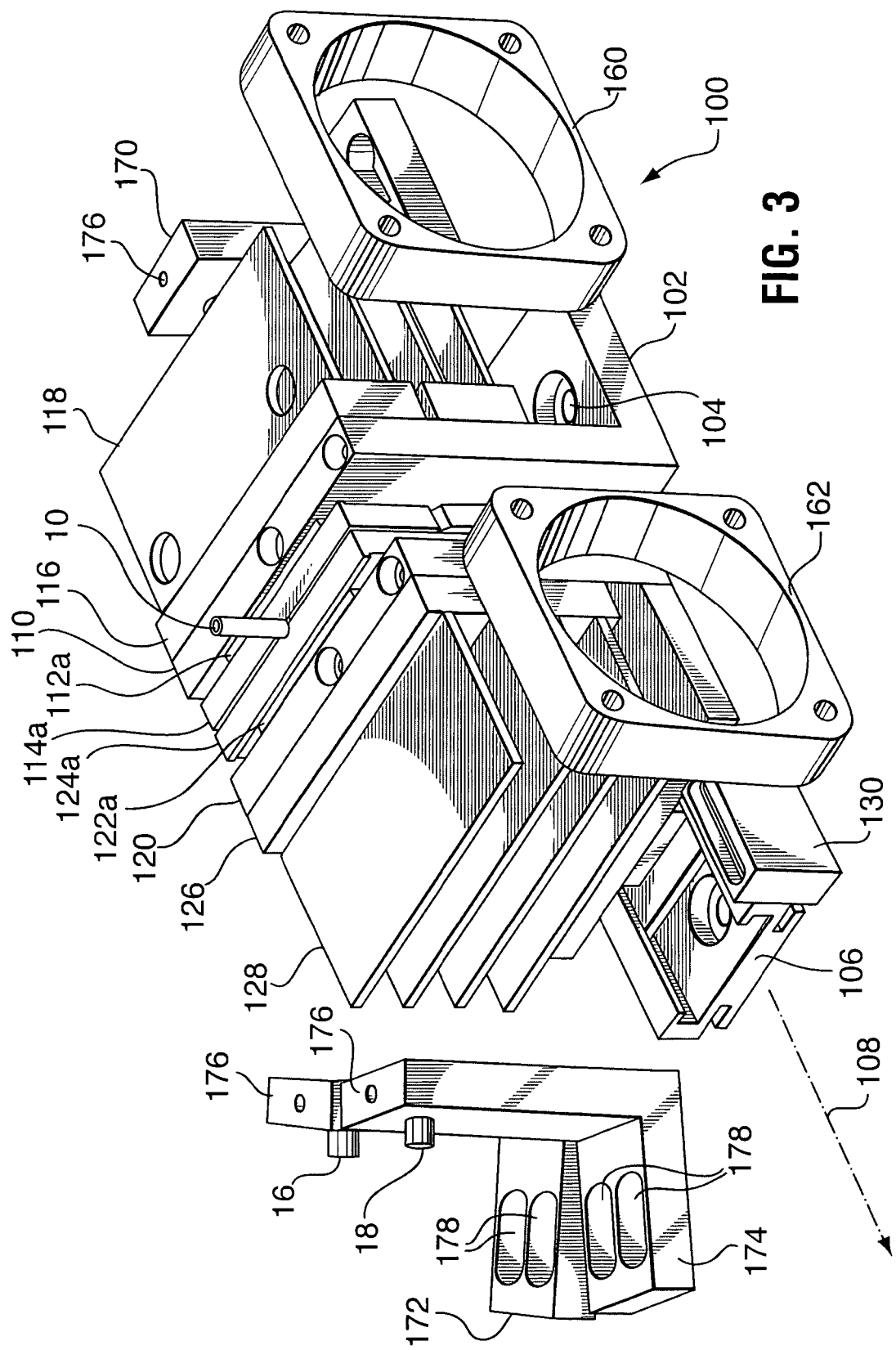
FIG. 3 is an isometric perspective view of a sample holder in accordance with a preferred embodiment of the present invention, shown in the closed, gripping position.

FIG. 3 illustrates the sample holder 100 in accordance with a preferred embodiment of the present invention. The sample holder 100 (also referred to herein as a sample-holding device) has a stationary base 102 which has a substantially flat underside for sitting upon a flat surface such as a workbench, lab counter, table, base plate or the like. The base preferably includes one or more bores through which a fastener could be inserted to securely mount the base to a base plate, table, workbench, lab countertop or the like. It is preferable that the base 102 of the sample holder 100 be securely attached to an immovable structure to improve measurement precision and to avoid having to frequently recalibrate the DLS system.

The base 102 preferably includes a rectilinear rail 106 defining a displacement axis 108. For manufacturability, the rail 106 and base 102 are preferably machined or cast as separate components and secured to each other by threaded fasteners (to thus define a "two-part base"). Alternatively, it would also be possible for the rail 106 to be made integral with the base 102 (to define a unitary base). In any event, the base 102 has a connected rail portion 106 that together supports the rest of the sample holder.

The sample holder 100 further includes an upright backing member 110 (i.e. a fixed, upright wall) and a movable clamping member 120 (i.e. a movable upright member) that can move relative to the backing member (or wall) 110 between an open, retracted position, in which the clamping member 120 no longer contacts the container 10 (i.e. the movable upright member and the wall are separated by a distance greater than an outer diameter of the container 10) and a closed, holding (or "gripping") position, in which the clamping member (movable upright member) 120 presses against the container 10 to lightly and gently clamp or hold the container 10 between the clamping member 120 (movable member) and the backing member (wall) 110 whereby the container 10 is immobilized for optical analysis of the fluid sample in the container 10. While the illustrated embodiments of the sample holder were designed for optical analysis such as DLS or QELS, the sample holder (or variants thereof) can also be used for static light scattering or as part of a spectrofluorometer. Preferably, the backing member 110 is integral with the base 102. Similarly, in the preferred embodiment, the movable member 120 is integrally formed with a horizontally disposed sliding plate 120a that engages and slides over the rail 106.

In a preferred embodiment, the movable upright member 120 slides relative to the stationary wall member 110, guided by the rail 106 so that the movable member 120 is constrained to translate along the displacement axis 108. The displacement axis 108, as shown in FIG. 3, is substantially perpendicular to the backing and clamping members 110, 120. While sliding, or translational, motion is preferred, the movable upright member 120 could also be made to rotate relative to the wall 110 using pivots or hinges. The movable upright member 120 could also be made to slide along a vertical axis or a different horizontal axis, i.e. an axis orthogonal to the illustrated displacement axis 108. Alternatively, the sample holder 100 could use compound motion (both rotation and translation) to open and close the clamping member relative to the fixed, upright wall member.

Figure 5:
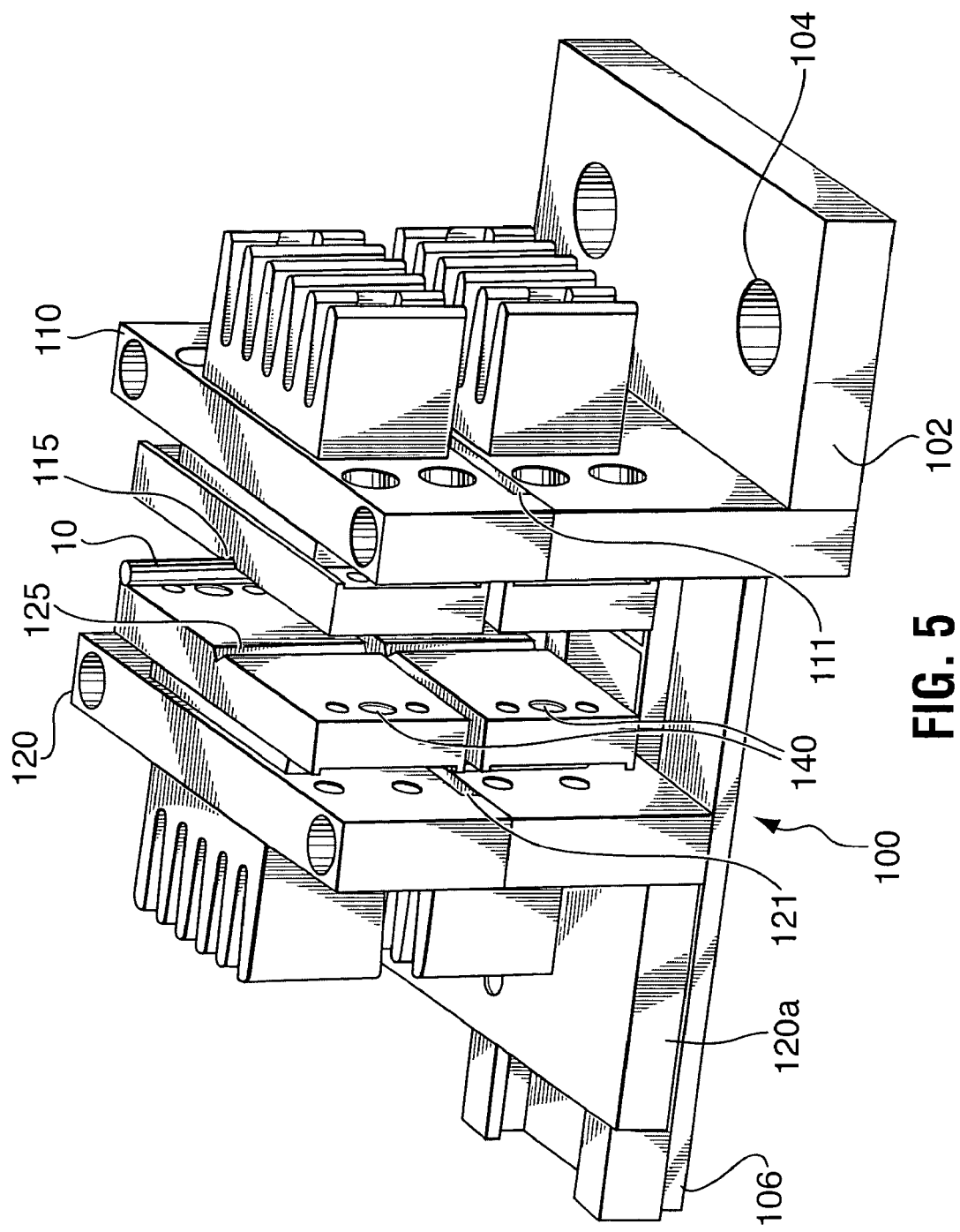
FIG. 5 is an isometric perspective view of the sample holder in accordance with another embodiment of the invention, shown in the open, retracted position.

The sample holder can further include a plurality of magnets 140 for biasing the movable member 120 toward the wall 110. Preferably, four pairs of cylindrical, oppositely poled magnets 140 are embedded in bores in the movable member (as shown in FIG. 5) and in the wall which thus provide a uniform magnetic force of attraction in substantial alignment with the displacement axis 108. The magnets 140 are designed to generate a magnetic force of attraction that, when the movable upright member is in the gripping position, is large enough to securely hold the container between the movable upright member and the wall but small enough to preclude deformation of the container and also small enough to enable a user to easily manually separate the movable upright member and the wall by manually forcing the movable upright member to the retracted position.

As shown in FIG. 3, the sample holder 100 can include a slider stopper 130, which can be secured to the rail 106 (or to the base plate) using one or more threaded fasteners (not shown). The slider stopper 130 limits the sliding displacement of the movable member 120 away from the wall 110. When the movable member reaches the slider stopper 130, the movable member is in the open, retracted position (which is shown in FIG. 5).

Figure 4:
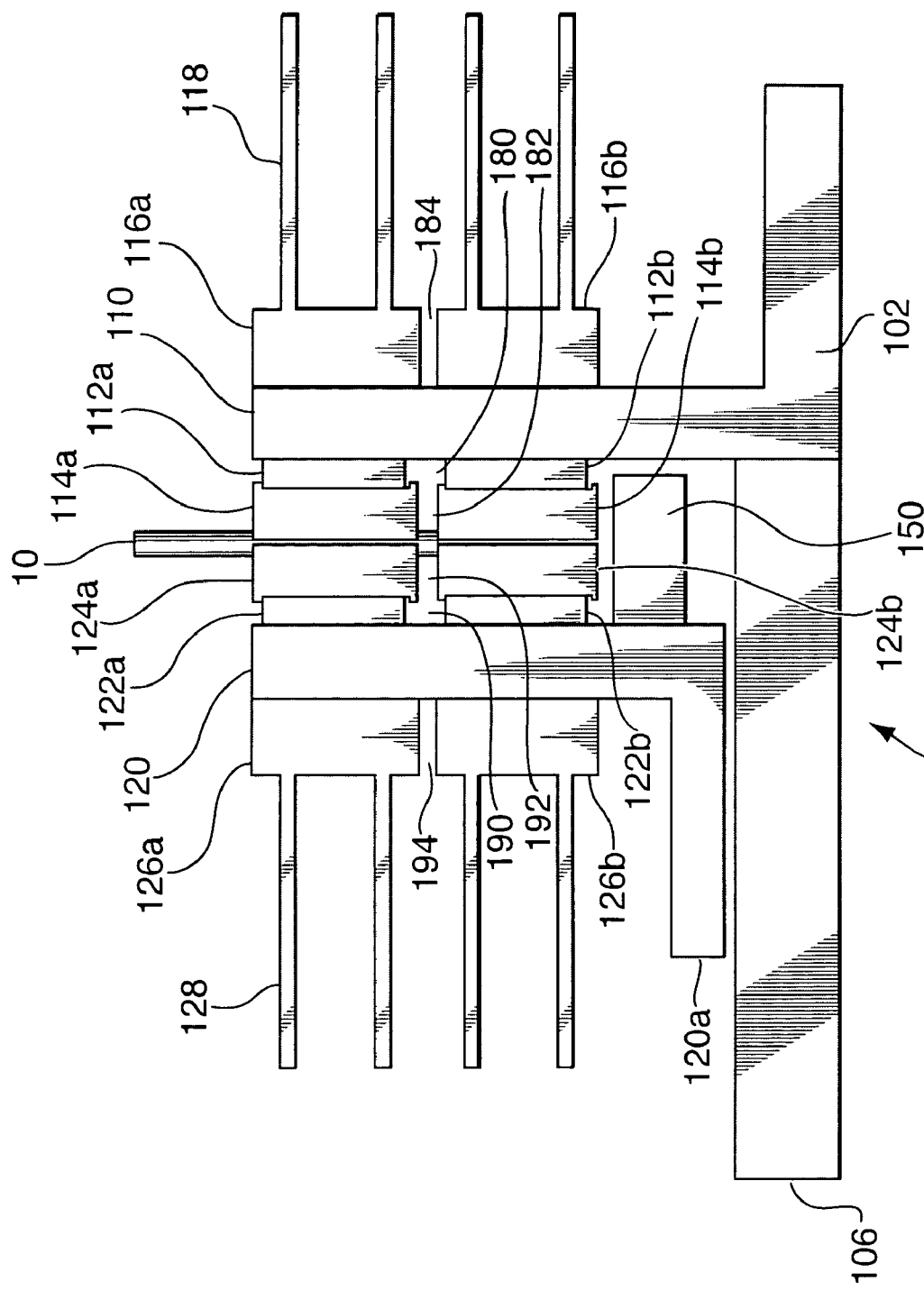
FIG. 4 is a side view of the sample holder shown in FIG. 3, but illustrated without the fans and fiber-holding brackets, also shown in the closed position.

FIG. 4 is a side elevational view of the sample holder 100 shown in FIG. 3, but depicted without the fans and fiber-holding brackets. As shown in FIGS. 3 and 4, the sample holder 100 has a first pair of vertically spaced-apart heating/cooling elements 112a, 112b connected to an inwardly facing surface of the backing member 110, the first pair of heating/cooling elements being capable of transferring heat to or from the fluid sample in the container 10. For the purposes of this specification, "vertically spaced-apart" means that there is an upper component and a lower component separated by a gap. Also for the purposes of this specification, "inwardly facing" means facing toward the sample container and thus "outwardly facing" means facing away from the sample container.

The sample holder 100 also includes a first pair of vertically spaced-apart heat-conductive plates 114a, 114b connected to inwardly facing surfaces of the first pair of heating/cooling elements 112a, 112b for conducting heat to or from the container to thus either cool or heat the fluid sample.

The sample holder 100 further includes a second pair of vertically spaced-apart heating/cooling elements 122a, 122b connected to an inwardly facing surface of the movable clamping member 120, the second pair of heating/cooling elements being capable of transferring heat to or from the fluid sample in the container 10. The sample holder 100 further includes a second pair of heat-conductive plates 124a, 124b connected to inwardly facing surfaces of the second pair of heating/cooling elements 122a, 122b for conducting heat to or from the container 10 to thus cool or heat the fluid sample. The heating/cooling elements can be attached to the movable member using studs and bores, threaded fasteners or other known mechanical fasteners. Likewise, the heat-conductive plates can be attached to the heating/cooling elements using studs and bores, threaded fasteners or other known mechanical fasteners.

To recap, therefore, there are four heating/cooling elements 112a, 112b, 122a, 122b and four attached plates 114a, 114b, 124a, 124b in the preferred embodiment, as shown in FIG. 4. The vertically spaced-apart pairs of heating/cooling elements define first gaps 180, 190. The vertically spaced-apart pairs of plates likewise define second gaps 182, 192. The first gaps 180, 190 are aligned with the second gaps 182, 192, as shown in FIG. 4. Furthermore, the wall 110 and the movable member 120 have substantially horizontal slots 111, 121 that also align with the gaps 180, 190, 182, 192 on either side of the device to minimally obstruct optical access to the fluid sample in the translucent container 10. Furthermore, as shown in FIG. 4, the sample holder 100 has upper and lower heat sinks 116a, 116b attached to the outwardly facing surface of the wall 110 as well as upper and lower heat sinks 126a, 126b attached to the outwardly facing surface of the movable member 120. The heat sinks can be attached to the wall and movable member using studs in bores, threaded fasteners or other known mechanical fasteners. As shown in FIG. 4, the upper heat sinks 116a, 126a are disposed above the slots 111, 121 in the wall 110 and movable member 120 while the lower heat sinks 116b, 126b are disposed below the slots 111, 121. This heat sink design also minimally obstructs optical access to the fluid sample in the container 10. These upper and lower heat sinks define on each side of the device third gaps 184, 194 which are also aligned with the first gaps 180, 190, the second gaps 182, 192 and the slots 111, 121.

Preferably, the heating/cooling elements 112, 122 are Peltier-type thermoelectric devices with microthermocouples for temperature sensing and feedback control. Peltier heater/cooler devices are also known in the art as thermoelectric modules. These Peltier-type thermoelectric modules are small solid-state devices that function as heat pumps. Usually, a Peltier device has a "sandwich" structure formed by two ceramic plates with an array of small Bismuth Telluride cubes ("couples") in between. When a DC current is applied to the device, heat is transferred from one side to the other, where it must be removed with a heat sink. By placing the "cold" side facing the heat-conductive plate, the sample can thus be cooled. If the current is reversed, the Peltier device heat is transferred to the inner side and this heats the sample. These Peltier thermoelectric modules enable the sample holder 100 to rapidly control the temperature of the sample, e.g. for bringing the sample to the desired temperature and for performing temperature cycling.

As noted above and shown in FIGS. 3 and 4, the sample holder 100 preferably includes heat sinks 116, 126 connected to outwardly facing surfaces of the wall and movable member, respectively. These heat sinks 116, 126 can include fins 118, 128, respectively. The fins can be horizontal (as shown in the embodiment of FIGS. 3 and 4) or vertical (as shown in the. embodiment of FIG. 5). In any event, the finned heat sinks cooperate with the Peltier devices to cool the fluid sample by drawing heat away from the hot side of the Peltier devices.

In a preferred embodiment, the sample holder 100 includes fans 160, 162 for further improving the cooling efficiency of the Peltier devices by augmenting convective heat transfer of the finned heat sinks. It should be noted that the fans could be part of the sample holder 100 or they could be separate components (but nonetheless part of the DLS system). It should be noted that it is preferable to have the fans to improve cooling efficiency but they are not essential.

As further shown in FIG. 3, the sample holder can include a plurality of fiber-holding brackets 170, 172, 174 for holding the optical fibers at the same height as the slots to ensure that the incident light hits the sample and that the scattered light from the sample can be captured by the light-collecting fibers 16, 18. The optical fibers have either a focusing or collimating lens to narrow the laser beam so that illuminated sample volume is small, i.e. ideally one or only a few coherence volumes. This requires the ends of the optical fibers to be one focal length away from the center of the sample. The fiber holders 170, 172, 174 are thus mounted relative to the sample in order to provide distances to the sample that are each equal to the focal length. In a preferred embodiment, a first L-shaped bracket 170 holds the optical fiber 6 connected to the laser diode 2 or other optical source (referring back to FIG. 1) whereas second and third L-shaped brackets 172, 174 hold the light-collecting fibers 16, 18, respectively. Other brackets would, of course, be provided if additional light-collecting fibers are to be used to capture scattered light. As shown in FIG. 3, each of the L-shaped brackets includes a top threaded bore 176 for receiving a set screw (not shown) which can be used to fix the optical fiber in the bracket to ensure alignment with the plane of the slots. As shown in FIG. 3, each of the L-shaped brackets also includes a footing with an oblong slot through which a fastener can be inserted to secure the brackets to a bench, table, counter, base plate or other such surface.

In this embodiment, only a single light source is used and scattered light is collected by a plurality of light collectors. For example, the light collectors can be spaced at 15-degree intervals from each other. In one configuration, one light collector could be set up at a 45-degree angle from the incident light with a second collector at a 60-degree angle (again with respect to the incident light). Alternatively, the light collectors (or additional collectors) could be set up at 30 and 90 degrees. However, it should be appreciated that multiple light sources could be used as well and the number of light collectors and their respective angles or positions could also be varied. The sample holder 100 therefore enables a researcher to simultaneously obtain measurements at one or more scattering angles.

As further shown in FIG. 4, the sample holder 100 can include an elevated footrest 150 securely connected to a bottom portion of the movable member 120. In one embodiment, the footrest 150 can be detachable or vertically adjustable to accommodate capillaries or cuvettes of different lengths. In another embodiment, the footrest could include its own heating/cooling element (e.g. Peltier device) to supplement the heating/cooling elements 112, 122 already described above.

FIG. 5 illustrates the sample holder 100 in accordance with another embodiment of the present invention, shown in the open, retracted position. FIG. 5 shows that the backing member 110 and the clamping member 120 include, respectively, first and second grooved plates 114, 124 facing each other in a generally parallel arrangement and having opposed, substantially vertical grooves 115, 125 for holding the fluid container 10 in a substantially vertical orientation. The plates 114, 124 could also have knurling or other surface finishing that enhances adherence to glass or plastic so as to promote gripping of the glass or plastic capillaries or cuvettes. As shown, the grooves 115, 125 could have V-shaped profiles to grip a variety of differently sized, elongated tubular or square containers, such as capillaries or cuvettes. V-shaped grooves are generally preferred because they promote excellent heat transfer to or from a variety of differently sized and differently shaped containers. Alternatively, the grooves could have semicircular or rectangular profiles to grip capillaries or cuvettes having substantially round or substantially square cross-sections. To optimize heat transfer efficiency, the grooves should provide a substantially exact fit with the capillary or cuvette, although an exact fit is of course not necessary. In other words, semicircular or rectangular grooves can also be used to hold variably sized containers. Preferably, the sample container 10 is a disposable, glass or plastic capillary with round or square geometry and having a diameter of about 2 mm and a volume of about 30 microliters, although the sample holder 100 is designed to accommodate a range of sizes and therefore these dimensions should not be considered as limiting the scope of the invention. As is known in the art, the sample is loaded by capillary action and then the bottom of the capillary is sealed. In one embodiment, the V-shaped grooves are adapted to grip a capillary having an outer diameter in a range of 1.7 to 3.5 mm.

A further advantage of this sample holder 100 is that the path length of the light is short compared to most prior art devices because both the light path through the air, the wall thickness and the diameter of the capillary or cuvette are reduced. A short path length is desirable for measuring highly concentrated samples because this diminishes the likelihood that scattered light will strike a second particle and be scattered a second time (a phenomenon known as "multiple scattering"). In the context of platelet quality management, improving measurement precision means that it is easier to determine when a platelet solution is still viable and when it is no longer effective. It also advantageously reduces handling since platelet solutions need not be diluted prior to measurement.

In another embodiment, which is not illustrated, the sample holder could have two movable and lockable members rather than one movable member and a stationary wall. In this embodiment, one of the movable lockable members is locked in place, the container placed in the sample holder next to the locked movable member and then the second (unlocked) movable member is then moved into engagement with the container to thereby hold the container in place at which point the second (unlocked) movable member can be locked as well.

The embodiments of the invention described above are therefore intended to be exemplary only. The scope of the invention is intended to be limited solely by the appended claims.

We claim:

1. A sample holder for holding a fluid container for performing optical analysis of a fluid sample contained within the fluid container, the holder comprising:
   a base having a backing member, said backing member having a first container abutting surface;
   a clamping member having a second container abutting surface, said clamping member being movable relative to the backing member between an open, retracted position, in which the clamping member no longer contacts the fluid container, and a closed, holding position, in which the first and second abutting surfaces press against the fluid container to lightly clamp the fluid container between the clamping member and the backing member whereby the fluid container is immobilized for optical analysis of the fluid sample in the fluid container, wherein the backing member and the clamping member each includes slots which are aligned to provide optical access to the fluid sample when held in the sample holder to enable collection of light at an angle oblique to light incident on the sample;
   a first heating/cooling element abutting an inwardly facing surface of the backing member, the first heating/cooling element being capable of transferring heat to or from the fluid sample in the fluid container;
   a first heat-conductive member connected to an inwardly facing surface of the first heating/cooling element for conducting heat to or from the fluid ample in the fluid container;
   a second heating/cooling element abutting an inwardly facing surface of the clamping member, the second heating/cooling element being capable of transferring heat to or from the fluid sample in the fluid container; and
   a second heat-conductive member abutting an inwardly facing surface of the second heating/cooling element for conducting heat to or from the fluid sample in the fluid container.

2. The sample holder as claimed in claim 1 wherein the backing member and the clamping member include, respectively, first and second grooved plates facing each other in a generally parallel arrangement and having opposed, substantially vertical grooves for holding the fluid container in a substantially vertical orientation.

3. The sample holder as claimed in claim 2 wherein the grooves have V-shaped profiles to grip an elongated tubular container.

4. The sample holder as claimed in claim 3 wherein the V-shaped grooves are adapted to grip a capillary having an outer diameter in a range of 1.7 to 3.5 mm.

5. The sample holder as claimed in claim 2 wherein the grooves have either rectangular or semicircular profiles to grip a cuvette having either a substantially square or round cross-section to thus provide a substantially exact fit for efficient heat transfer.

6. The sample holder as claimed in claim 1 wherein the clamping member slides relative to the backing member along a displacement axis that is substantially perpendicular to the backing and clamping members.

7. The sample holder as claimed in claim 6 wherein the base comprises a rail for guiding the clamping member along the displacement axis.

8. The sample holder as claimed in claim 7 wherein the clamping member and backing member comprise magnets for magnetically biasing the clamping member toward the backing member.

9. The sample holder as claimed in claim 1 wherein the first and second heating/cooling elements are Peltier-type thermoelectric modules.

10. The sample holder as claimed in claim 1 wherein the slots are substantially horizontal.

11. The sample holder as claimed in claim 10 wherein the backing member and clamping member each further comprises upper and lower heat sinks connected to an outwardly facing surface of the backing and clamping members respectively above and below the horizontal slots.

12. The sample holder as claimed in claim 11 further comprising fans for blowing air over finned portions of the heat sinks.

13. The sample holder as claimed in claim 1 further comprising:
   a first pair of upper and lower heating/cooling elements connected to an inwardly facing surface of the backing member, the first pair of heating/cooling elements being capable of transferring heat to or from the fluid sample in the container;
   a first pair of upper and lower heat-conductive plates connected to an inwardly facing surface of the first pair of heating/cooling elements for conducting heat to or from the fluid sample in the container;
   a second pair of heating/cooling elements connected to an inwardly facing surface of the clamping member, the second pair of heating/cooling elements being capable of transferring heat to or from the fluid sample in the container; and
   a second pair of heat-conductive plates connected to an inwardly facing surface of the second pair of heating/cooling elements for conducting heat to or from the fluid sample in the container.

14. The sample holder as claimed in claim 13 wherein the clamping member and the backing member comprise horizontal slots aligned with gaps between the pairs of heating/cooling elements and heat-conductive plates to provide optical access to the fluid sample.

15. The sample holder of claim 1, further comprising at least one light source which directs a beam of light at the fluid sample within the container while the container is held by the sample holder, at least one light collector positionable in at least one of a plurality of positions around the sample holder and which collects light scattered by the fluid sample, and a correlating device that correlates collected scattered light to size and shape of particles suspended in the fluid sample.

16. The sample holder of claim 15, further comprising a single said light source and a plurality of said light collectors deployed around the sample-holding device to collect light scattered by the fluid sample.

17. The sample holder of claim 16, wherein the plurality of said light collectors are arranged at evenly spaced intervals around the sample holder.

18. The sample holder of claim 17, wherein said light collectors are arranged at 15 degree intervals around the sample holder.

19. The sample holder of claim 15, wherein the light source comprises a laser diode and the light collector comprises at least one optical fiber which captures scattered photons, the optical fiber being connected to a single-photon counter that generates and transmits TTL (transistor-transistor logic) pulses to the correlating device.

20. The sample holder of claim 19, further comprising a first mounting support which supports at least a first optical fiber connected to the laser diode, and at least a second mounting support which supports at least a second optical fiber connected to the single-photon counter.

21. The sample holder of claim 20, wherein the first and second mounting supports include substantially L-shaped brackets.

22. The sample holder of claim 15, further comprising a first fan for blowing air over a finned portion of a heat sink affixed to the backing member and a second fan for blowing air over a finned portion of a heat sink affixed to the clamping member.

23. A holding device for holding a fluid container capable of containing a fluid sample for undergoing optical analysis, the holding device comprising:
a base having a container abutting wall;
a clamping member having a container abutting surface and capable of moving relative to the wall between a retracted position, in which the clamping member and the wall are separated by a distance greater than an outer diameter of the fluid container, and a holding position, in which the fluid container is held between the container abutting surface and the container abutting wall, wherein the container abutting wall and the clamping member each comprise a slot, the slots being aligned for providing optical access to the sample to enable collection of light at an angle oblique to light incident on the sample;
a first heating/cooling element disposed on an inwardly facing surface of the wall;
a second heating/cooling element disposed on an inwardly facing surface of the clamping member;
a first heat-conductive member connected to an inwardly facing surface of the first heating/cooling element, the first member having an inwardly facing groove for gripping the container over a substantial surface of the container for efficiently conducting heat to or from the container; and
a second heat-conductive member connected to an inwardly facing surface of the second heating/cooling element, the second member having an inwardly facing groove for gripping the container over a substantial surface of the container for efficiently conducting heat to or from the container.

24. The holding device as claimed in claim 23 wherein the base comprises a rectilinear rail for guiding the clamping member when sliding relative to the wall.

25. The holding device as claimed in claim 23 wherein the clamping member and the wall hold the container in a substantially vertical orientation.

26. The holding device as claimed in claim 25 further comprising:
a first pair of upper and lower Peltier-type thermoelectric devices connected to an inwardly facing surface of the wall;
a first pair of upper and lower heat-conductive plates connected respectively to the upper and lower thermoelectric devices for holding the container and conducting heat to or from the container;
a second pair of upper and lower Peltier-type thermoelectric devices connected to an inwardly facing surface of the movable member; and
a second pair of upper and lower heat-conductive plates connected respectively to the upper and lower thermoelectric devices for holding the container and conducting heat to or from the container;
wherein the upper and lower thermoelectric devices and respective upper and lower plates on both the wall and the clamping member define gaps that are aligned with the slots in the wall and clamping member to provide optical access to the fluid sample when held in the sample holder.

27. The holding device as claimed in claim 26 wherein the clamping member is magnetically biased toward the wall by a magnetic force of attraction that, when the clamping member is in the holding position, is large enough to securely hold the container between the clamping member and the wall but small enough to preclude deformation of the container and also small enough to enable a user to easily manually separate the clamping member and the wall by manually forcing the clamping member to the retracted position.

28. The holding device as claimed in claim 23 wherein the clamping member is magnetically attracted toward the wall by a magnetic force that is large enough to securely hold the container between the clamping member and the wall but small enough to preclude deformation of the container and also small enough to enable a user to easily manually separate the clamping member and the wall by manually forcing the clamping member to the retracted position.

29. The holding device as claimed in claim 23 further comprising at least one fan for blowing air over finned portions of heat sinks affixed to the wall and clamping member.

30. The holding device of claim 23, further comprising at least one light source which directs a beam of light at the fluid sample within the container while the container is held by the holding device, at least one light collector positionable in at least one of a plurality of positions around the holding device and which collects light scattered by the fluid sample, and a correlating device that correlates collected scattered light to size and shape of particles suspended in the fluid sample.

31. The holding device of claim 30, further comprising a single said light source and a plurality of said light collectors deployed around the sample-holding device to collect light scattered by the fluid sample.

32. The holding device of claim 31, wherein the plurality of said light collectors are arranged at evenly spaced intervals around the sample holder.

33. The holding device of claim 32, wherein said light collectors are arranged at 15 degree intervals around the sample holder.

34. The holding device of claim 30, wherein the light source comprises a laser diode and the light collector comprises at least one optical fiber which captures scattered photons.

35. The holding device of claim 34, wherein the optical fiber is connected to a single-photon counter that generates and transmits TTL (transistor-transistor logic) pulses to the correlating device.

36. The holding device of claim 34, further comprising a first mounting support which supports at least a first optical fiber connected to the laser diode, and at least a second mounting support which supports at least a second optical fiber connected to the single-photon counter.

* * * * *